United States Patent
Kia

(10) Patent No.: US 9,597,047 B2
(45) Date of Patent: *Mar. 21, 2017

(54) DIGITAL RADIOGRAPHIC DEVICE HAVING A LINEAR SCANNER

(71) Applicant: Omid Ebrahimi Kia, Potomac, MD (US)

(72) Inventor: Omid Ebrahimi Kia, Potomac, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/201,526

(22) Filed: Jul. 4, 2016

(65) Prior Publication Data

US 2016/0310089 A1 Oct. 27, 2016

Related U.S. Application Data

(63) Continuation of application No. 14/846,746, filed on Sep. 5, 2015, now Pat. No. 9,380,989, which is a continuation of application No. 14/194,683, filed on Mar. 1, 2014, now Pat. No. 9,125,571, which is a continuation of application No. 13/164,661, filed on Jun. 20, 2011, now Pat. No. 8,662,749.

(60) Provisional application No. 61/372,917, filed on Aug. 12, 2010.

(51) Int. Cl.
*H05G 1/02* (2006.01)
*A61B 6/00* (2006.01)
*G01N 23/04* (2006.01)
*A61B 6/03* (2006.01)
*A61B 6/06* (2006.01)

(52) U.S. Cl.
CPC ............. *A61B 6/4452* (2013.01); *A61B 6/03* (2013.01); *A61B 6/032* (2013.01); *A61B 6/06* (2013.01); *A61B 6/5205* (2013.01); *A61B 6/547* (2013.01); *G01N 23/04* (2013.01)

(58) Field of Classification Search
CPC ... A61B 6/4441; A61B 6/4405; A61B 6/4452; A61B 6/035; A61B 6/4476; A61B 6/587
See application file for complete search history.

(56) References Cited

U.S. PATENT DOCUMENTS 6,609,826 B1 * 8/2003 Fujii .................... A61B 6/12
378/197

* cited by examiner

*Primary Examiner* — Hoon Song
(74) *Attorney, Agent, or Firm* — Esmael Dinan; David G. Grossman

(57) ABSTRACT

An apparatus comprises a first detector mounted on a sliding bar and an electromagnetic source including a collimator to generate an exposure window. The apparatus comprises a control system configured to slide linearly the first detector along the sliding bar and synchronously move the collimator to direct the exposure window to the first detector. The movements of the exposure window are registered to movements of the first detector.

20 Claims, 9 Drawing Sheets

DIGITAL RADIOGRAPHIC DEVICE HAVING A LINEAR SCANNER

CROSS-REFERENCE TO RELATED APPLICATIONS

This application is a continuation of application Ser. No. 14/846,746, filed Sep. 5, 2015, which is a continuation of application Ser. No. 14/194,683, filed Mar. 1, 2014, which is a continuation of application Ser. No. 13/164,661, filed Jun. 20, 2011, now U.S. Pat. No. 8,662,749, which claims the benefit of U.S. Provisional Application No. 61/372,917, filed Aug. 12, 2010, which is hereby incorporated by reference in its entirety.

FIELD OF THE INVENTION

The present invention is in the field of digital x-ray imaging. More particularly, the present invention is related to a system and method for a digital radiographic device having a linear scanner sweeping an x-ray beam during an imaging operation.

BACKGROUND OF THE INVENTION

Traditionally, x-ray images were created on film whereby the x-rays would interact with the film or a scintillation material that would accelerate the development of the film material. After a curing process the image on the film would turn permanent for analysis by Radiologists. Film based methods are usually coined analog x-ray imaging. Real-time x-ray imaging is increasingly being utilized by medical procedures as therapeutic technologies advance. Real-time, digital x-ray image acquisition is preferable to the use of film because digital imaging eliminates film processing and related chemicals and takes advantage of the improved performance and reduced costs provided by modern image sensor technology.

A number of real-time x-ray imaging systems are known. X-ray detectors span a large range of products. These include fluoroscope-based systems where x-rays are projected into an object to be x-rayed and shadows caused by relatively x-ray opaque matter within the object are detected on the fluoroscope located on the opposite side of the object from the x-ray source.

More recently image intensifiers are used to aid in Fluoroscopy and Cinematography type of acquisitions whereby x-rays are first converted to an electron stream and then accelerated in the large tube. The electron stream is then targeted onto a phosphorous material that would render an image. An analog or digital camera is then matched to this port for image capture. Currently flat panel detectors are commonplace whereby the incident x-rays are first converted to light via a scintillation layer and a light detector captures the incident exposure. Similar to the flat panel detectors, there are a class of direct conversion material that can convert the incident x-ray flux to electronic signal without having to go to the intermediary such as visible light. Computed Radiography is yet another method of x-ray detection that is farther removed from the methods described above. This method utilizes a material that stores the amount of x-ray flux within its constituent material. Then a scanner is used to read out the material and later erase the residual information.

U.S. Pat. Nos. 4,587,668 and 6,863,439 introduce a device that patients can step into and take an x-ray image of their foot. There are two primary modes of imaging: aposteriori and lateral (aka top down and sideways). Current devices take these images by x-ray film, by flat panel detectors and by registering the x-ray arm with the imaging plane to achieve the different modes of acquisition.

Current digital x-ray acquisition systems require large sensors which add to the complexity and cost of the x-ray imaging system. Additional complexity for taking aposteriori and lateral images should be addressed without adding complexity to the x-ray device. Therefore, there is a need to develop a system and method for digital x-ray imaging with a reduced complexity, cost, and equipment size. Furthermore, such a system should be able to produce x-ray images from various angles from aposteriori to lateral positions. It is an object of the present invention to address this issue and to provide a system and method for x-ray imaging and provide substantial benefit to the medical industry. These aspects are the primary derivative of the embodiments of this invention.

BRIEF SUMMARY

It is an object of the present invention to provide a method and system for a digital x-ray imaging device. The device may include a platform 901 connected to a frame 902, a sliding bar 903, a first detector 907 mounted on the sliding bar 903, an x-ray source 905, and a control system 208. The x-ray source 905 may include a collimator 904 to generate an x-ray exposure window. The first detector 907 may interface with a processor that processes x-ray image data received from the first detector 907, and may generate at least one x-ray image from the x-ray image data. The control system is configured to slide the first detector 907 along the sliding bar 907 and synchronously move the collimator 904 to direct the x-ray exposure window to the first detector 907. The x-ray exposure window movements may be registered to the first detector 907 movements.

The first detector 907 may interface with a processor that processes x-ray image data received from the first detector 907, and may generate at least one x-ray image from the x-ray image data. The generated x-ray image length may be substantially equal to scanning range of the x-ray exposure window. The processor may control the movement of the first detector 907 along the sliding bar 903. The first detector 907 may slide horizontally along the sliding bar 903 in lateral orientation or aposteriori orientation, while the x-ray exposure window scans the platform 901. The x-ray source 905 may be able to rotate laterally around the platform 901. The speed of scanning depends on available dose output from the x-ray source or the first detector 907 readout limits.

It is additionally an object of the present invention to provide a system and method for x-ray imaging, wherein the x-ray source 905 is connected to the first detector 907 by an arm 906 and moving synchronously with the first detector 907. The x-ray source movements may be registered to the first detector 907 movements. The arm 906 extending from the x-ray source 905 to the first detector 907 may force a rigid registration of the x-ray exposure window incident on the first detector 907. The first detector 907, the arm 906, and the x-ray source 905 may be tied together so that when the x-ray source 905 and the arm 906 rotate from lateral orientation to aposteriori orientation, the first detector 907 rotates with the arm 906.

It is a further object of the present invention to provide a method and system for x-ray imaging, wherein the first detector is positioned in the aposteriori orientation and is tied to an arm and the x-ray source when taking images in aposteriori orientation. The apparatus may further include a second detector positioned in the lateral orientation, which is tied to the arm and the x-ray source when taking images in lateral orientation.

In an example embodiment, the x-ray source may be fixed while the collimator moves to direct the x-ray exposure window to the first or the second detector. In another example embodiment, the first or second detector may be a TDI detector. The TDI detector may include a TDI sensor interfacing a circuit board. The TDI sensor may include at least one CMOS or CCD strip containing at least one column and a plurality of rows coupled with a scintillator to convert x-rays into visible light. The TDI sensor may be a narrow strip with a substantially higher length than width. The TDI sensor length may be in the range of 120 mm to 250 mm.

It is a further object of the present invention to provide a method for x-ray imaging. The method may include generating an x-ray exposure window using an x-ray source including a collimator. Further the method may include sliding a first detector mounted on a sliding bar connected to a frame along the sliding bar and synchronously move the collimator to direct the x-ray exposure window to the first detector. The collimator movements may be registered to the first detector movements. The x-ray exposure window scans a platform connected to the frame. Further, the method may include processing x-ray image data received from the first detector, and generating at least one x-ray image from the x-ray image data.

The x-ray source may be connected to the first detector by an arm and moving synchronously with the first detector, wherein the x-ray source movements are registered to the first detector movements. The first detector, the arm, and the x-ray source may be tied together so that when the x-ray source and the arm rotate from lateral orientation to aposteriori orientation, the first detector rotates with the arm.

These and other objects and features of the present invention will become more apparent from the following detailed description of the present invention considered in connection with the accompanying drawings which disclose an embodiment of the present invention. It should be understood, however, that drawings, as well as the description, are presented here for the purpose of illustration only and not as a definition of the limits of the invention.

BRIEF DESCRIPTION OF THE SEVERAL VIEWS OF THE DRAWINGS

The accompanying drawings, which are incorporated in and form a part of the specification, illustrate an embodiment of the present invention and, together with the description, serves to explain the principles of the invention.

DETAILED DESCRIPTION OF EMBODIMENTS

The embodiments of the present invention provide digital x-ray imaging using a linear scanner. In an example embodiment, the device may include a platform connected to a frame, a sliding bar, a first detector mounted on the sliding bar, an x-ray source, and a control system. The x-ray source may include a collimator to generate an x-ray exposure window. The first detector may interface with a processor that processes x-ray image data received from the first detector, and may generate at least one x-ray image from the x-ray image data. The control system is configured to slide the first detector along the sliding bar and synchronously move the collimator to direct the x-ray exposure window to the first detector. The x-ray exposure window movements may be registered to the first detector movements.

The x-ray device may utilize a linear scanner to achieve the imaging portion of the device by integrating fine control of the detector and the x-ray aperture together in a way that captures the needed anatomy. The detector could be a part of a digital camera. The cameras could reconfigure the component that captures the signal and convert it to an electronic signal. This type of reconfiguration may require an implementation of some high level functionality. Functionality such as changing binning, frame rate, exposure levels and other mainstream functionality lies within the domain of the camera.

A camera may employ a sensor or a detector, which interacts with the physical neighborhood and generates a set of electrical signals in response to the physical conditions. A sensor may implement functionalities such as pixel pitch, number of pixels, technology family (CCD, CMOS, direct conversion and others) and light conversion amongst other factors. Each and every implementation includes unique features and demands a set of functionality to make it work. For example, a CCD sensor may require an external Analog to Digital Conversion unit and a CMOS sensor could fully embed almost all electronic components right on the device requiring only a minimal set of components. Detectors may require some sort of timing and line driving circuitry, which could be generated, from a timing logic component. The electronic signal converted from some sort of radiation could be resident as an analog signal which may be required to be converted to digital, hence a system would require an Analog to Digital Conversion. Some systems convert these signals to digital and store them locally until an external unit requests for the data requiring some sort of memory storage. Cameras may provide some automation and some workflow implementation, which may require a resident processor. Beyond these devices, a set of analog devices such as resistors, capacitors, inductors, amplifiers and associated devices is needed to complete a camera.

Figure 1:
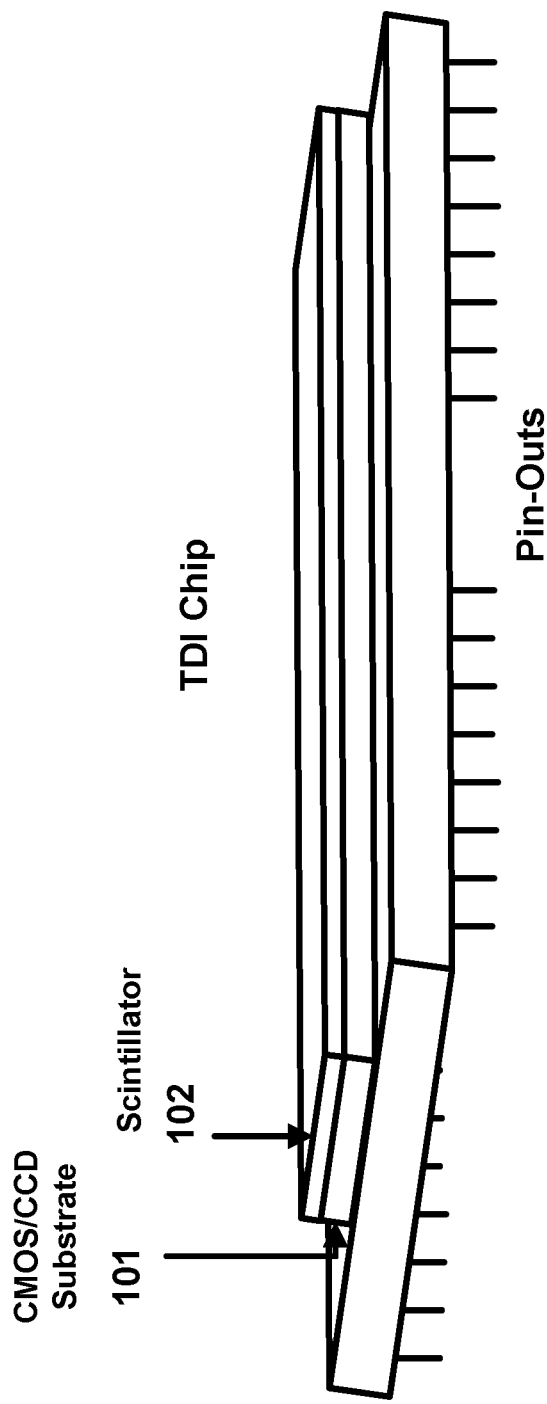
FIG. 1 is an illustration showing an exemplary TDI sensor with CMOS/CCD strip according to one aspect of the illustrative embodiments.

FIG. 1 is an illustration showing an exemplary TDI sensor with CMOS/CCD strip 101 according to one aspect of the illustrative embodiments. CMOS/CCD strip 101 may contain a few columns and many rows coupled with scintillator 102 to convert x-rays into visible light and may pin to interface to a suitable circuit board. A TDI (Time Delay Integration) camera may be used along with a pivoting x-ray source matched to the x-ray sensitive portion of the camera. The X-ray source utilizes a thin slit to collimate the output x-ray to a very thin slit (typically) 28 inches away. By pivoting the x-ray source synchronously with the detector, a swath of area can be scanned.

Figure 2:
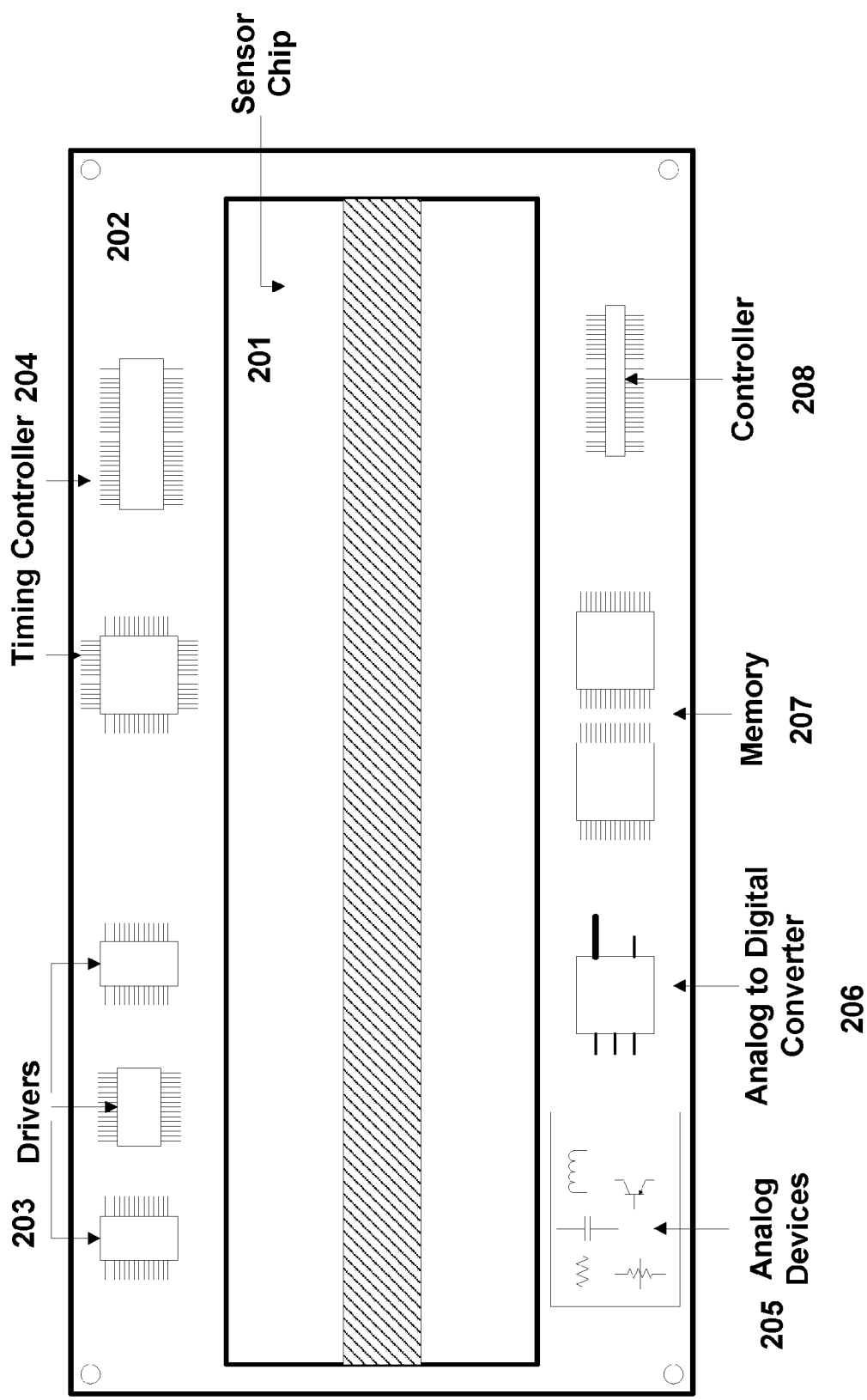
FIG. 2 is a schematic diagram showing an exemplary TDI Camera according to one aspect of the illustrative embodiments.

FIG. 2 is a schematic diagram showing an exemplary TDI Camera according to one aspect of the illustrative embodiments. In an example TDI camera, the TDI sensor 201 is interfaced with a set of electronics on a circuit board 202 to provide a higher level of functionality than is provided directly from the sensor. In this example, drivers 203, timing controller 204, analog devices 205, A/D converter 206, memory chips 207 and a microcontroller 208 may be interfaced on a single circuit board 202. Alternatively, components could be added or removed to this board to and from other parts of a potential product.

Typically, a thin detector may be suitable to minimize stand-off distance to which the patient needs to stand on. Large format thin detectors able to cover the whole foot or hand may be costlier than smaller detectors. Thick detectors may have to include a larger clearance height adding to patient discomfort. The middle ground may be to utilize a small enough detector with a scanning capacity to achieve the desired field of view while achieving the cost constraints.

An additional factor is the image quality. Taking large format images at known dose per frame setting may allow integration of photons directly in the image detector. When multiple images are taken at linearly less flux, image quality may be degraded mostly due to high noise levels at lower flux levels and larger readout noise. This combination of scanning and image quality may be achieved with the x-ray based TDI sensors where the scanning element and the photon integration component is both implemented in the electronics. Using TDI sensors, the same image quality may be achieved as if it were a large format sensor. Furthermore, current large format sensors may employ amorphous silicon, amongst others, which may not be as efficient as their CCD or CMOS equivalents. This may be due to the difficulty of implementing large format CCD or CMOS detectors. However, TDI sensors that rival the equivalent large format sensors may be of the CCD or CMOS flavors. Currently, TDI sensors are high quality, low cost detectors that could be implemented for large format imaging. Also current TDI cameras could have resolution as low as 27 um per pixel, which is lower than the large format detectors.

The detectors may operate to generate images such as Radiographs, Fluoroscopic or Cinematographic images which may differ by their refresh rates and their exposure control mechanisms. There is another class of image formation, which deviates from the simplistic mindset and at times is referred to as computed imaging. The computed parts could either be done as a post-processing element or during the acquisition. Tomography forms the basis of these types of imaging with modalities such as Pan Tomography, Linear Tomography, Circular Tomography or Computed Tomography form the more prevalent modes of operation. These modalities could aim to target a specific focus upon an anatomy of interest, which then may lend itself to the particular mode of operation. For example, the Pan Tomography creates a single image representing the continuous and curved arch of the human jaw and Computed Tomography represents all possible focal layers within the field of view.

Of particular interest is how the Pan Tomography image is generated. The focal layer could be achieved by matching the motion of a small slit of x-ray incident on a detector with the motion of the gantry, which could orbit the subject. By using a travelling slit, radiography could be generated representing a cut in space centered on a panoramic arch. Extension of this concept could lead to a digital detector whereby the travelling slit of x-ray flux could be captured on the CCD/CMOS detector. The same detector could generate simple radiographs of the head for Cephlometric analysis by designing a focal trough that could encapsulate the extent of the head. A detector that could capture an image as described is called a Time Delay Integration (TDI) sensor. Other applications such as remote sensing applications may also use a TDI sensor for its higher level of sensitivity. This detector may have many rows and some finite number of columns but the data is read out one column at a time. During each read out time, the device transfers the stored charge of one column to a neighboring column where by subsequent exposure to the scene would continue its flux integration.

A column could be read one at a time and an image may be formed after many columns are read out. Another extension is utilization of the TDI sensor in frame mode whereby the full field of the TDI sensor is readout frame by frame. That is instead of reading one column at a time, the whole sensor could be readout at a time.

Cost of equipment may increase with size of sensor. TDI and line scan detector being much less costlier than their full field counterparts such as the flat panel detectors or image intensifier based solutions. TDI sensors could also boast an improvement in image quality with respect to a one shot radiograph. The process of integration could be done in software whereby a TDI sensor operating as a frame-based camera generates slit images that could be integrated in software to create the whole image. Advances in detector technology is making the quality of the resultant images comparable but in general TDI sensors tend to generate better images than those integrated in software but lack the post processing capability to correct for the inaccuracies in focusing.

The x-ray detector may interface with a processor that processes x-ray image data received from the first detector, and may generate at least one x-ray image from the x-ray image data. The generated x-ray image length may be substantially equal to scanning range of the x-ray exposure window. The processor may control the movement of the first detector along the sliding bar. The first detector may slide horizontally along the sliding bar in lateral orientation or aposteriori orientation, while the x-ray exposure window scans the platform. The speed of scanning depends on available dose output from the x-ray source or the first detector readout limits.

Utilization of a TDI sensor may require matching of the sensor motion with respect to the sensor readout speed. The focused image plane may be matched with the sensor. A processor could take into account the characteristics of the TDI sensor such as binning mode, and pixel and column clock rate and match them to the motor that moves the sensor. The processor further may transfer the readout lines once at a time to a holding area so that a resultant image representative of a radiograph is created. Other processing elements such as automatic exposure control could take place to match the dynamic range of the incoming energy with the detective capability of the sensor.

To enable a proper medical imaging device, a processing element is required to interface with the unit to not only start the scan but also to read out the scan and manage it throughout the medical analysis process. The resultant image may be wrapped around a DICOM transport envelope to be used later.

The detector could detect a partial view of the desired anatomy. To image the interested anatomy some sort of image formation may be required. This could be achieved by moving the detector to cover a larger area as opposed to the detector itself. A TDI detector could form the eventual image by matching the movement of the detector with the detector readout speed. Bigger detectors, which read in frame mode, could also achieve the same by either stitching individual images or integrating the TDI functionality in software.

In an example embodiment, based on the amount of x-ray flux needed to generate sufficient image quality, the detector movement speed could be back calculated. This may be done considering accumulation of sufficient amount of exposure. This then could lead into how fast the detector has to be read out. A processor may command the motors and the detector together to achieve the overall imaging objective. The movement commands may be generated based on the physical mapping of platform traversal and the motor configuration so that the processor knows ahead of time how much travel occurs with an associated command. The same relationship to physical travel may be calculated for the detector whereby the pixels of known size have to be read out. Therefore the processor may read out the detector in a way that matches the physical distance with respect to the readout commands. The platform travel command could be calculated with respect to the detector readout speed.

The image plane may be considered when making this relationship. If the image plane of interest is at the detector surface, then the speed of the platform matches that of the detector width readout. This may be one pixel wide in case of the TDI sensor and may be the width of the detector for frame readout detectors. If for any reason a different image plane is required the two speeds could be different. The relationship may be based on layer that needs to be focused and may consider the magnification of the plane since the x-ray source is very close to a point source.

The registration of the x-ray exposure window with the detector may start with standard regulation which may state that the x-ray radiation is required to be confined to the extent of the detector. The width of the radiation may be smaller but not larger. The size of the width directly affects the focal trough and signal to noise ratio of the resultant image. The focal trough may be required to be larger than the dimensions of the anatomy of interest. The speed of the scan could have the same limitation. A faster scan could have a much wider focal trough with a lower signal to noise ratio characteristics. The scanning process may provide a large scan field for an otherwise small detector. Since the x-ray exposure window is limited to the detector then the exposure window may be required to follow the detector. This could be done by either registering the x-ray head with its internal collimator with the detector or moving the two of them together. Another option is to move the x-ray head on its own independent set of rails but link the detector and x-ray supply motion by electronic means. An either linear x-ray head motion, rotation of the x-ray head or motion of the collimator could implement the motion of the x-ray supply head, which is to be matched with the linear motion of the detector.

X-ray is at times coined an art of shadow imaging. Since x-ray penetrates one could acquire a varying level of shadows that have travelled across an anatomy of interest. Other similar diagnostic techniques exist by merely using a different wavelength in the overall Electro-Magnetic range of frequencies. An example method is utilization of a Radio Frequency based radiation and another is utilization of an Infrared band of light. The premise being that a scanning process could augment a small field of view detector to render a high field of view image.

Figure 3:
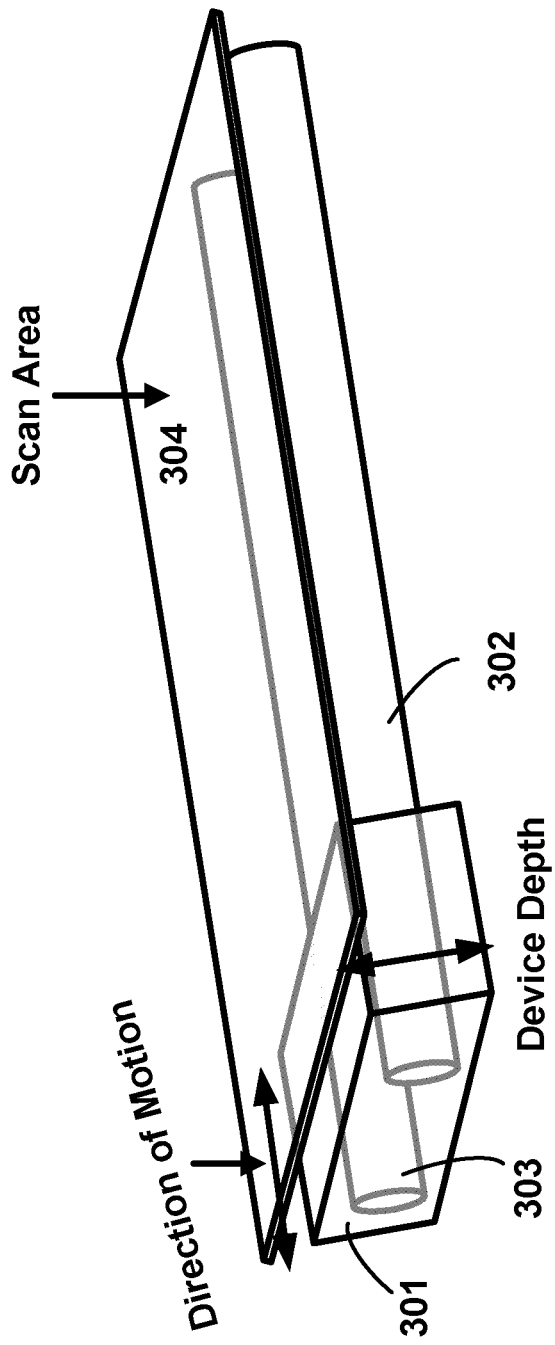
FIG. 3 is a schematic diagram depicting an example of the relative movement of the detector across the sliding bars according to one aspect of the illustrative embodiments.

FIG. 3 is a schematic diagram depicting an example of the relative movement of the detector across the sliding bars 302 and 303 according to one aspect of the illustrative embodiments. TDI camera 301 mounted on a pair of rails 302 and 303. The rectangular plate depicting the camera 301 slides across the sliding bars 302 and 303 while scanning to achieve the shown Scan area 304. Since the camera 301 is thin, the effective device depth could be very small.

The TDI sensor could be mounted on rails on the foot support mechanism. The rails 302 and 303 move the sensor in a scanning sweep. Typical lengths of TDI sensors may be 120-150 mm in length. There could be large number of variations that may extend the length up to 250 mm. This detector is then moved precisely on the rails 302 and 303 and an image arbitrary in length could be formed. These cameras could be made as thin as possible since they do not require bulky lens elements.

In an example embodiment, the X-ray source could be registered to the TDI sensor's strip in both Lateral and Aposteriori orientations. The arm extending from the x-ray to the TDI camera may force a rigid registration of the beam incident on the sensor. The x-ray apparatus may be registered to the camera element so that the camera slit is exposed. Speed of the scanning could allow very fast scanning to around a few seconds per image. The speed of the scan predominantly depends on the available dose output from the x-ray source and the detector readout limits. TDI cameras could be highly efficient detectors may require very low power x-ray sources. This could allow for a large degree of cost reduction to be realized.

In another example embodiment, the x-ray source is connected to the first detector by an arm and moving synchronously with the first detector. The x-ray source movements may be registered to the first detector movements. The arm extending from the x-ray source to the first detector may force a rigid registration of the x-ray exposure window incident on the first detector. The first detector, the arm, and the x-ray source may be tied together so that when the x-ray source and the arm rotate from lateral orientation to aposteriori orientation, the first detector rotates with the arm. A camera may rotate from lateral to aposteriori orientation. They could be tied together so that when the x-ray arm rotates the detector rotates with the arm.

In another example embodiment, a method for x-ray imaging is provided. The method may include generating an x-ray exposure window using an x-ray source including a collimator. Further the method may include sliding a first detector mounted on a sliding bar connected to a frame along the sliding bar and synchronously move the collimator to direct the x-ray exposure window to the first detector. The collimator movements may be registered to the first detector movements. The x-ray exposure window scans a platform connected to the frame. Further, the method may include processing x-ray image data received from the first detector, and generating at least one x-ray image from the x-ray image data.

Figure 4:
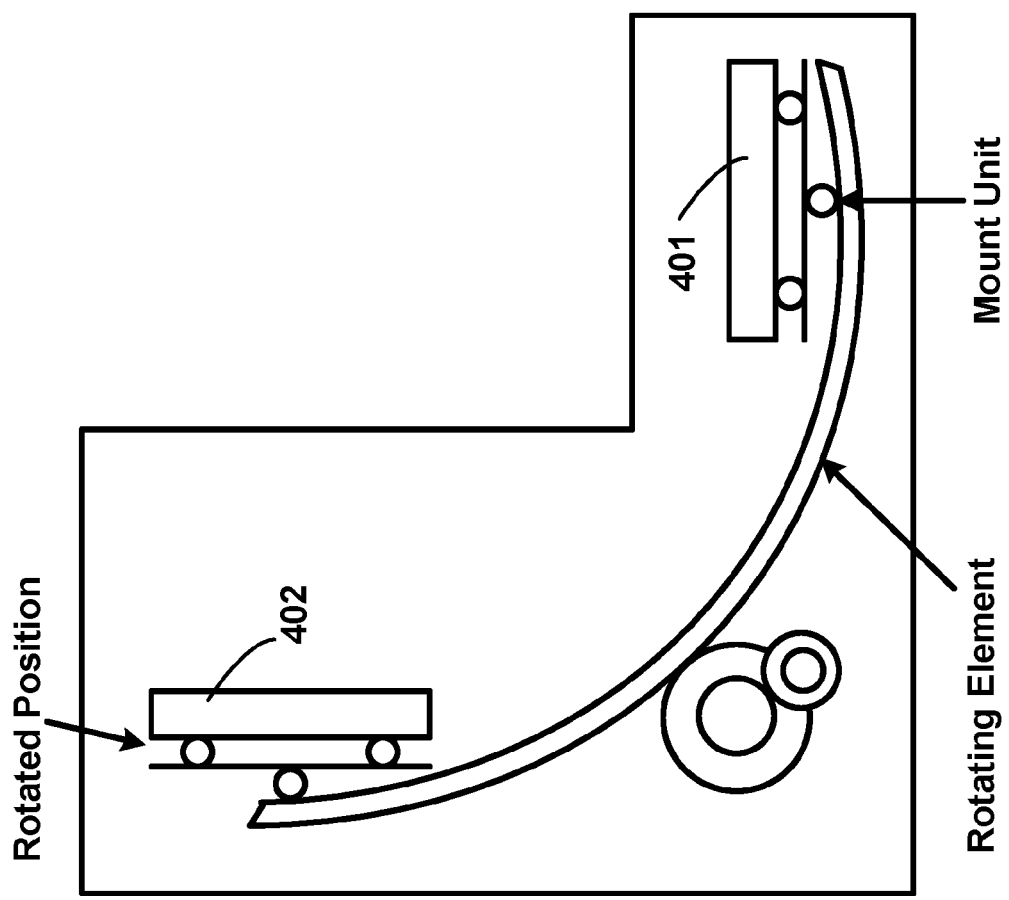
FIG. 4 is a depiction of a camera switching between lateral and aposteriori orientation according to one aspect of the illustrative embodiments.

FIG. 4 is a depiction of a camera switching between lateral and aposteriori orientation according to an example embodiment. In this example, a first detector 402 is positioned in the aposteriori orientation and is tied to an arm and the x-ray source when taking images in aposteriori orientation. The apparatus may further include a second detector 401 positioned in the lateral orientation, which is tied to the arm and the x-ray source when taking images in lateral orientation.

A number of benefits could be attained. We can build in an automatic exposure control mechanism whereby a read out column is used to change the x-ray characteristic to increase or decrease output dose. Based on the readout speed and number of output columns, the TDI sensor focuses on a certain layer in space. A configuration of x-ray to detector distance along with scanning speed and readout speed could be used to widen the focal trough to provide a traditional radiograph. Similarly, the focal trough could be narrowed down. This could provide a Tomosynthesis capture of the field. This setup could also be adapted to other small part scanning.

Figure 5:
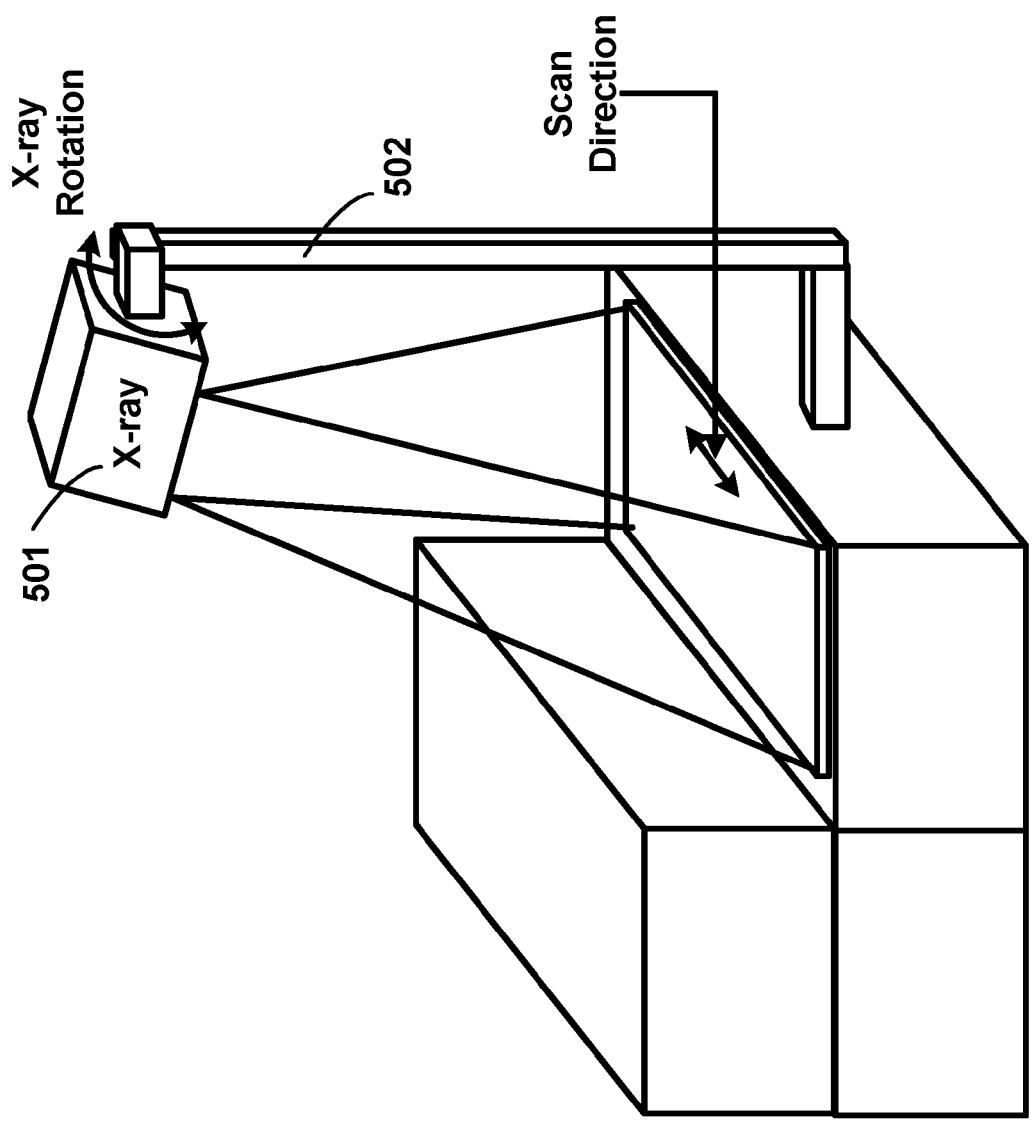
FIG. 5 is a schematic diagram illustrating a rotatable x-ray head according to one aspect of the illustrative embodiments.

FIG. 5 is a schematic diagram illustrating a rotatable x-ray head 501 in an example embodiment. The x-ray source may be fixed while the collimator moves to direct the x-ray exposure window to the first or the second detector. A rotatable x-ray head 501 may be used instead of sliding the x-ray head. In another example embodiment, a fixed x-ray with a moving collimator may be used. The x-ray arm 502 could be fixed to the device and the scanning mechanism is derived by rotating the x-ray head. Alternatively, the scanning mechanism could be achieved by fixating the x-ray head and moving collimation so that it would match to the active region of the TDI sensor.

Figure 6:
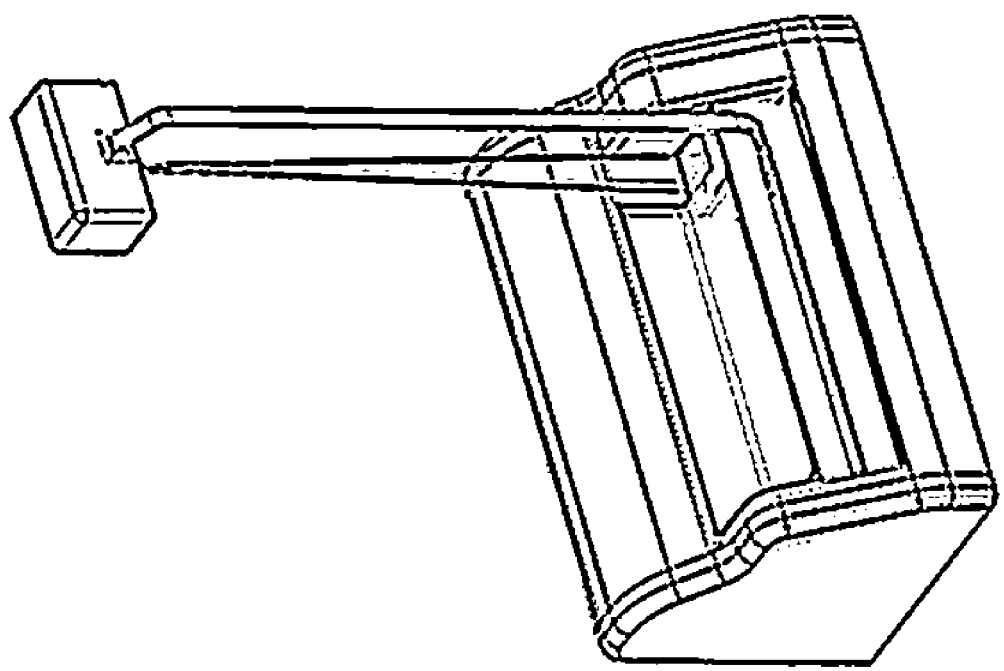
FIG. 6 is an illustration showing an exemplary x-ray diagnostic system according to the present invention.
Figure 7:
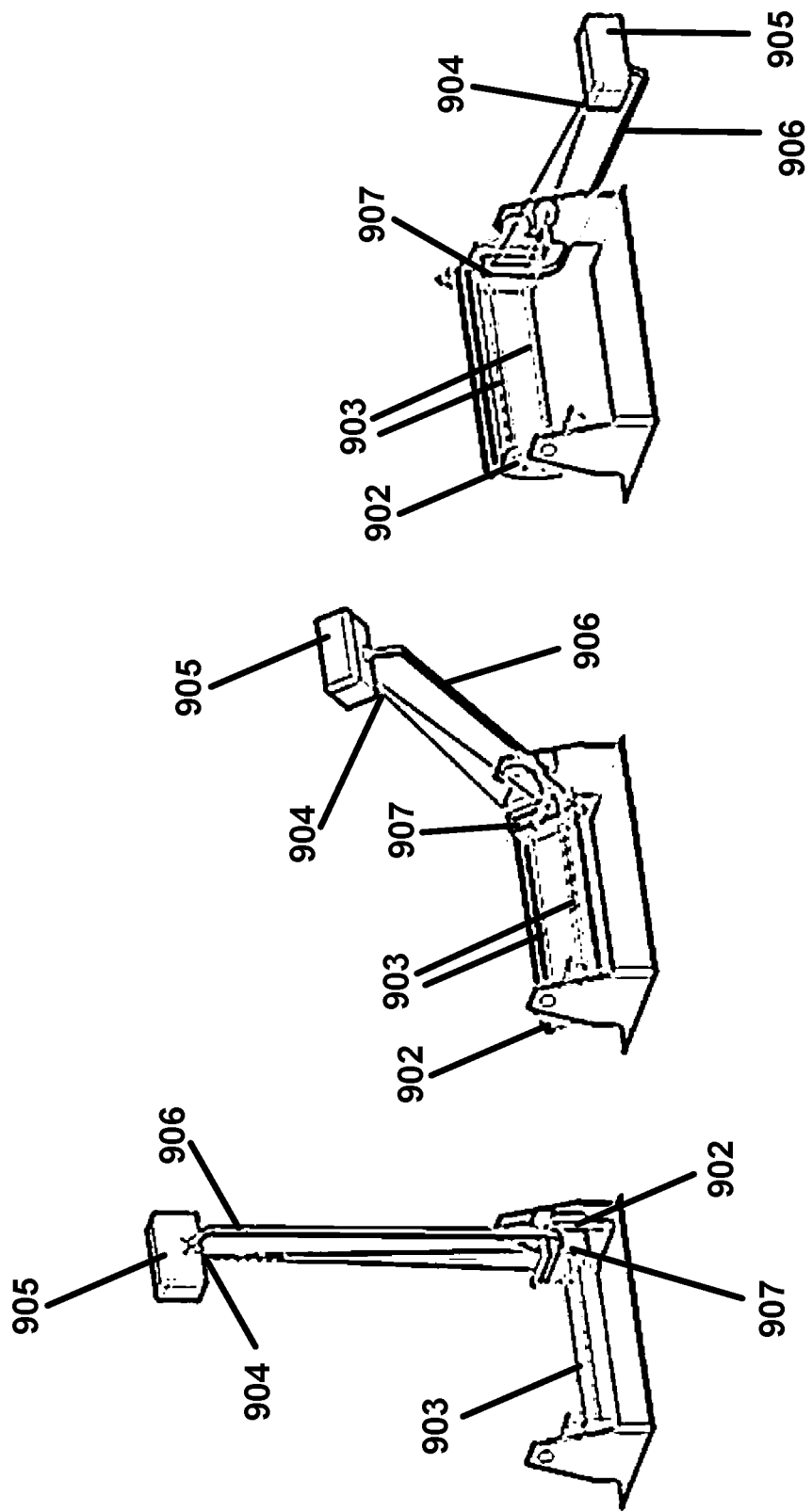
FIG. 7 is an illustration depicting the rotation of the device from lateral to aposteriori position according to one aspect of the illustrative embodiments.

FIG. 6 is an illustration showing an exemplary x-ray diagnostic system. This particular example embodiment capitalizes on a rigid registration of the x-ray arm with a fixed x-ray slit to the camera. FIG. 7 is an illustration depicting the rotation of the device from lateral to aposteriori position according to one aspect of the illustrative embodiments. The x-ray source, the arm, and the detector rotate together. The arm implements a rigid registration between the detector and the x-ray source.

Figure 8:
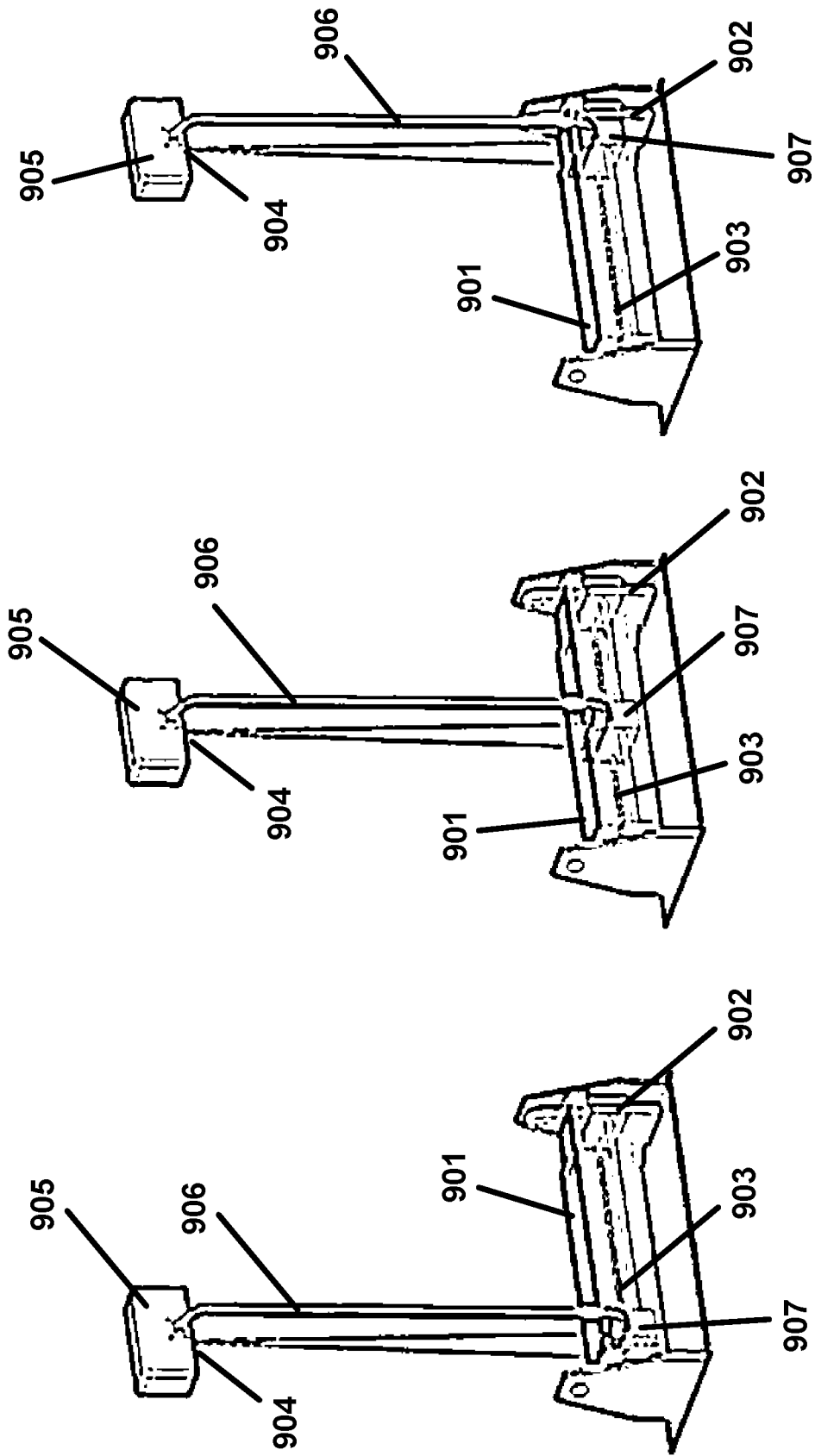
FIG. 8 is an illustration depicting x-ray scanning in lateral position according to one aspect of the illustrative embodiments.
Figure 9:
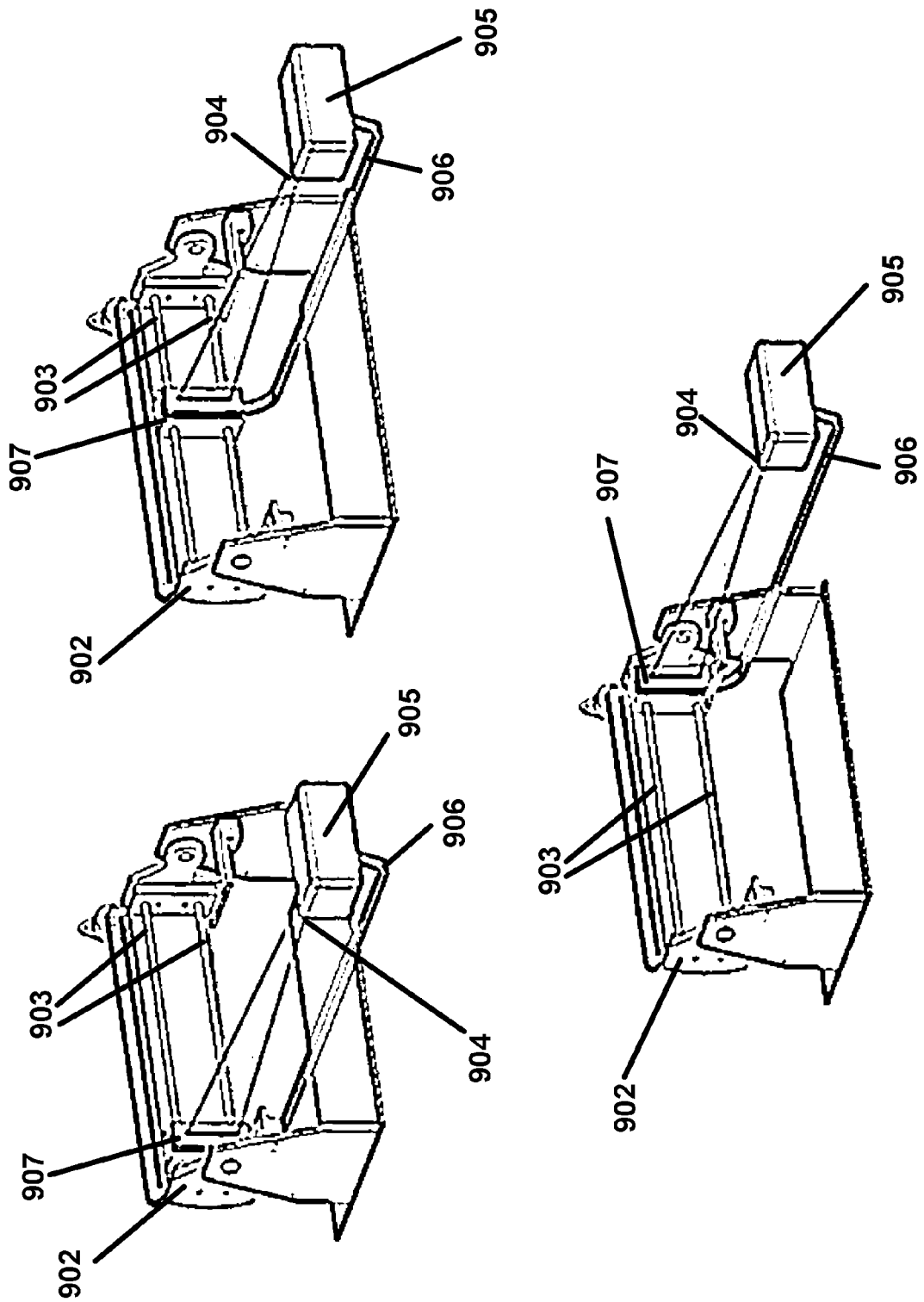
FIG. 9 is an illustration depicting x-ray scanning in aposteriori position according to one aspect of the illustrative embodiments.

FIG. 8 is an illustration depicting x-ray scanning in lateral position, and FIG. 9 is an illustration depicting x-ray scanning in aposteriori position according to one aspect of the illustrative embodiments. These figures depict example set of motions and orientations. These drawings show the inner workings of this embodiment in terms of range of movements, orientations and driving mechanisms.

The system described above could be used for Podiatry application. The device could be installed on the floor of a laboratory for a patient to step on. Mechanical design guidelines could be followed to reduce the form factor of the device by methods such as placing the scanning motor in parallel with the sliding bars instead of below the sliding bars. Mounting guidelines such as boring a small opening in the floor of the laboratory could further reduce the height requirements so that a patient could easily step on the device. Since this type of Podiatry scanning does not require imaging of a moving part it is possible to implement a linear scanning methodology to achieve the imaging objective.

The example embodiments as shown are configurable to image the anatomies of interest. Allowing long enough strokes in the sliding bars could easily accommodate length of the foot. Placement of the foot and angulations of the x-ray allows oblique angles to image the ankle regions as well. This type of device could be modified for imaging of the hand and could be configured as a small desktop unit.

The method of scanning described above along with appropriate x-ray techniques allows for an adequate diagnostic capability of common problems such as ligation and bone problems. Similar diagnostic capability is also available in machines such as X-ray Film, Computed Radiography, Digital Radiography and Computed Tomography. Several multimodality imaging such as Ultrasound and Magnetic Resonance are capable of performing studies other than ligation and bone problems such as venous studies. The purpose of this machine is to provide a cost effective and generic imaging that is comparable to X-ray film, Computed Radiography and Digital Radiography type of imaging. The benefit of this invention is the cost factor and the small footprint achievable by use of a TDI sensor where the small form factor along with cost savings for a small scanning field of view is achieved. This type of design also lends itself to use a smaller x-ray head further reducing cost. The TDI sensor with a small active region for imaging could be used to scan the foot rather than image the foot in one whole step.

An example source to object distance is 28 inches. The device could operate at 15 to 60 inches with sufficient x-ray conversion efficiencies that allows diagnostic image quality.

In this specification, "a" and "an" and similar phrases are to be interpreted as "at least one" and "one or more."

Many of the elements described in the disclosed embodiments may be implemented as modules. A module is defined here as an isolatable element that performs a defined function and has a defined interface to other elements. The modules described in this disclosure may be implemented in hardware, software, firmware, wetware (i.e hardware with a biological element) or a combination thereof, all of which are behaviorally equivalent. For example, modules may be implemented as a software routine written in a computer language (such as C, C++, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies are often used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) podiatry digital x-ray device.

However, one skilled in the art will recognize that embodiments of the invention could be applied to many other x-ray digital imaging applications such as x-ray devices for imaging hands, elbows or other body parts.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. An apparatus for tomography imaging, the apparatus comprising:
    a first detector mounted on a bar;
    an x-ray source comprising a collimator to generate an x-ray exposure window; and
    a control system configured to cause:
        linear movement of the first detector along the bar;
        rotational movement of the first detector, the bar and the x-ray source around the linear movement of the first detector;
        move synchronously the collimator to direct the x-ray exposure window to the first detector; and
        register the exposure window to movements of the first detector.

2. The apparatus according to claim 1, wherein the linear movement of the first detector and the rotational movement of the first detector move the first detector from a first orientation to a second orientation.

3. The apparatus according to claim 2, wherein the first orientation is one of a lateral orientation and an aposteriori orientation.

4. The apparatus according to claim 2, wherein the second orientation is one of a lateral orientation and an aposteriori orientation.

5. The apparatus according to claim 1, wherein the x-ray source is rotatable.

6. The apparatus according to claim 1, wherein the x-ray source is pivotable.

7. The apparatus according to claim 1, further comprising a second detector.

8. The apparatus according to claim 7, further comprising a rotating element coupled to both the first detector and the second detector.

9. The apparatus according to claim 7, wherein the second detector is rotatable.

10. The apparatus according to claim 1, wherein the control system is further configured to cause the first detector to generate at least one tomography image.

11. The apparatus according to claim 1, wherein a tomography slice is derived as a focal trough configuration.

12. The apparatus according to claim 1, wherein the first detector interfaces with a processor, the processor processing x-ray image data received from the first detector, and generating at least one x-ray image from the x-ray image data.

13. The apparatus according to claim 1, wherein the first detector horizontally slides along the bar in lateral orientation or aposteriori orientation, while the x-ray exposure window scans a platform.

14. The apparatus according to claim 1, wherein the x-ray source is connected to the first detector by an arm and moves synchronously with the first detector.

15. The apparatus according to claim 14, wherein the arm extending from the x-ray source to the first detector causes a rigid registration of the x-ray exposure window incident on the first detector.

16. The apparatus according to claim 14, wherein the first detector, the arm, and the x-ray source are tied together so that when the x-ray source and the arm rotate from lateral orientation to aposteriori orientation, the first detector rotates with the arm.

17. The apparatus according to claim 1, wherein the first detector is positioned in an aposteriori orientation and is tied to an arm and the x-ray source when taking images in aposteriori orientation, the apparatus further including a second detector positioned in a lateral orientation and is tied to the arm and the x-ray source when taking images in lateral orientation.

18. The apparatus according to claim 1, wherein the x-ray source is fixed while the collimator moves to direct the x-ray exposure window to the first detector.

19. The apparatus according to claim 1, wherein the first detector is a TDI detector.

20. The apparatus according to claim 19, wherein the TDI detector includes a TDI sensor interfacing a circuit board, the TDI sensor comprising at least one CMOS or CCD strip, the at least one CMOS or CCD strip containing a at least one column and a plurality of rows coupled with a scintillator to convert x-rays into visible light.

* * * * *